United States Patent [19]

Farquharson et al.

[11] Patent Number: 4,888,174

[45] Date of Patent: Dec. 19, 1989

[54] INSECTICIDAL POLYMERIC COMPOSITIONS

[75] Inventors: Richard A. Farquharson, Houston; Edwina B. Mitchell, Pearland, both of Tex.

[73] Assignee: The Dow Chemical Company, Midland, Mich.

[21] Appl. No.: 220,185

[22] Filed: Jul. 18, 1988

Related U.S. Application Data

[63] Continuation-in-part of Ser. No. 110,236, Oct. 19, 1987, abandoned, which is a continuation-in-part of Ser. No. 945,424, Dec. 22, 1986, abandoned.

[51] Int. Cl.$^4$ .................... A01N 25/00; A01N 25/34; A01N 57/00; A61K 31/74
[52] U.S. Cl. ..................... 424/405; 424/78; 424/416; 514/89
[58] Field of Search ............ 424/78, 81, 416, 409, 424/405; 514/89

[56] References Cited

U.S. PATENT DOCUMENTS

| | | | |
|---|---|---|---|
| 2,899,771 | 10/1958 | Burris, Jr. | 43/124 |
| 2,952,938 | 2/1957 | Abrams | 43/131 |
| 3,244,586 | 4/1966 | Rigterink | 167/33 |
| 3,408,323 | 10/1965 | Hackney | 260/45.85 |
| 3,928,564 | 12/1975 | Cardarelli | 424/83 |
| 4,102,991 | 7/1978 | Krydonieus | 424/27 |
| 4,400,374 | 8/1983 | Cardarelli | 424/78 |
| 4,430,468 | 2/1984 | Schumacher | 424/109 |
| 4,678,684 | 7/1987 | Sand | 424/78 |

OTHER PUBLICATIONS

Encyclopedia of Chemical Technology, 3rd Ed., vol. 17, Pigments, John Wiley & Sons, Inc., New York, pp. 790–864 (1982).
Int. Biodeterior, Bull., vol. 14, Issue 4, pp. 123–127 (1978) (CA 90:187697f).
Kun Chung Hsueh Pao, vol. 21, Issue 1, pp. 27–34 (1978) (CA 89:1664u).
Japanese 59/18,822 (Derwent 84–060162).
Japanese 48/83,139 (Derwent 74–33389V).
Australian 83/16,980 (Derwent 84–062988).
Japanese 58/169,810 (Derwent 84–013607).
Japanese 59/42,709 (Derwent 84–097524).
Japanese 59/141,506 (Derwent 81–235081).
Pr. Inst. Technol. Drewna, vol. 16, Issue 3, pp. 91–114 (1969) (CA 73:54942j).
Down Earth, vol. 37, Issue 1, pp. 16–21 (1980) (CA 94:97958v).
J. Econ. Entomol., vol. 67, Issue 6, pp. 721–727 (1974) (CA 82:69173u).
Kyushu Byogaichu Kenkyukai Ho, vol. 27, pp. 162–164 (1981) (CA 96:81296h).
Pest Contr., vol. 40, Issue 7, pp. 20, 22, 43 (1972) (CA 77:148485x).
Japanese 58/25,012 (Derwent 83-28669k).

*Primary Examiner*—Douglas W. Robinson
*Assistant Examiner*—Raymond J. Henley, III
*Attorney, Agent, or Firm*—Craig E. Mixan; Ronald G. Brookens

[57] ABSTRACT

The rate of migration of O-halopyridyl phosphate insecticides from polyethylene articles is retarded. Incorporation of a copolymer having a comonomer which is an unsaturated 3 to 5 carbon atom carboxylic acid, or a derivative thereof, decreases the rate of insecticide loss from such articles, particularly films.

4 Claims, No Drawings

INSECTICIDAL POLYMERIC COMPOSITIONS

CROSS REFERENCE TO RELATED APPLICATION

This application is a continuation-in-part of Ser. No. 110,236, now abandoned, filed Oct. 19, 1987, which is a continuation-in-part of Ser. No. 945,424, filed Dec. 22, 1986, now abandoned.

BACKGROUND OF THE INVENTION

This invention relates to novel polymeric insecticidal compositions with improved, longer-lasting, insecticidal properties. It also relates to a method for retarding the migration of insecticides which have been incorporated into polymeric articles. This invention further relates to a method for protecting certain crops from insect damage by application of polymeric articles prepared by the method of the present invention.

In known procedures for protecting fruits and vegetables from insect damage, insecticides are sprayed multiple times on the fruits or vegetables during the growing season. Such procedures have the disadvantage of adding pesticides to the environment which do not reach the targeted fruit or vegetable crop. Further, the persons applying the spray are exposed to the non-target pesticide spray. With particular crops, such as date palms where the fruit can be as high as 25 feet or more above the ground, the difficulty of isolating the persons applying the spray from the non-target spray is even more difficult due to the need to use high pressure spraying equipment. To overcome these disadvantages, insecticides have been incorporated into polymeric articles, which in turn are applied to the crops or in the vicinity thereof, thus reducing exposure of both the environment and the applicator to unnecessary quantities of active ingredients.

In methods where O-halopyridyl phosphate-containing polymer films are employed, such films suffer the problem of having the insecticide migrate too quickly from the film. Migration is defined to mean that the insecticide moves or diffuses to the surface of the polymer film where it is volatilized. This rapid migration of the O-halopyridyl phosphate insecticide decreases the concentration of insecticide present in the polymer, thus reducing the effectiveness of shrouds, bags or film produced therefrom for controlling insects.

SUMMARY OF THE INVENTION

It has been unexpectedly discovered that the addition of relatively small amounts of selected 3 to 5 carbon atom carboxylic acid comonomers, such as acrylic acid or methacrylic acid, to certain polymer blends containing an O-pyridyl phosphate insecticide will significantly retard the migration of the O-halopyridyl phosphate insecticide from such polymers, thus maintaining the ability of articles, including films, formed from such polymers to control insects over a longer period of time.

The present invention provides an insecticidal polymeric composition which comprises:

(a) an O-halopyridyl phosphate insecticide of the formula:

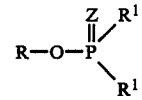

wherein R represents halopyridyl, Z represents a member of the group consisting of oxygen and sulfur, and $R^1$ represents a member of the group consisting of lower alkoxy, amino and lower alkylamino; and (b) a blend of homopolymer low density polyethylene (LDPE) and of an ethylene copolymer, wherein the ethylene copolymer has at least one comonomer which is an unsaturated 3 to 5 carbon atom carboxylic acid, salt or ester thereof, and the comonomer of said ethylene copolymer is present in a concentration effective to retard the migration of said O-halopyridyl phosphate insecticide from films derived from said composition; and (c) an effective amount of a UV stabilizer.

Another embodiment of the present invention is an insecticidal polymeric composition comprising:

(a) an O-halopyridyl phosphate insecticide;

(b) a blend of homopolymer low density polyethylene (LDPE) and of an ethylene copolymer, wherein the comonomer of said ethylene copolymer is selected from the group consisting of the carboxylic acid, salt or ester of acrylic acid or methacrylic acid, and said comonomer is present in a concentration effective to retard the migration of said O-halopyridyl phosphate from films derived from said composition; and (c) an effective amount of an ultraviolet light stabilizer.

The comonomer concentration in the composition of the present invention can range from about 0.5 to about 20 percent by weight of the total composition, preferably from about 2 to about 8 percent by weight, most preferably from about 3 to about 5 percent by weight.

The concentration of O-halopyridyl phosphates should be effective to control insects within the locus of films derived from said composition. The O-halopyridyl phosphate insecticide is present in the compositions of the present invention in insecticidally effective amounts. Such amounts can be in a concentration of about 0.1 to about 15 percent by weight of the composition, preferably from about 1 to about 2 percent by weight of the composition.

The present invention is also directed to a method for retarding the migration of an O-pyridyl phosphate insecticide from a low density polyethylene matrix by incorporating into the matrix, an ethylene copolymer having at least one comonomer which is an unsaturated 3 to 5 carbon atom carboxylic acid, salt or ester thereof present in a concentration to effectively retard the migration of the O-halopyridyl phosphate insecticide from the polymer matrix.

Another embodiment of the invention includes articles such as, for example, sheets, films or shrouds prepared from the insecticidal polymeric compositions by conventional processing operations such as molding, shaping, extruding, calendering or the like. The articles may optionally contain (d) an opaque pigment to retard or encourage exposure of the fruit to direct sunlight. The articles may be either unperforated or perforated to allow air to more freely circulate around the fruit or vegetable.

The present invention is also directed to a method for protecting fruit from moisture and insect damage, comprising applying a film or shroud, as described hereinbefore, to a maturing fruit or vegetable.

The present invention has the advantages of eliminating spraying operations of the fruit or vegetables, while still maintaining insect control as good as or better than those methods previously taught. Thus, aerial pesticidal exposure to the spray applicator and to non-target areas is eliminated. The present invention also has the advantage of reducing the levels of pesticide which are present in or on the fruit, since multiple spraying operations are no longer necessary, and the amount of the pesticide to which the fruit is directly exposed is far less than by conventional spraying operations.

DETAILED DESCRIPTION OF THE INVENTION

The term "shroud" is meant to refer to an insecticide-containing polymeric article that covers, screens or guards the fruit or vegetable to be protected. The shroud can be open at the bottom or closed liked a bag. Preferably the shroud is open-bottomed. The shroud can be either a film which is wrapped around the fruit or vegetable or a tubular sleeve which is slipped over the vegetable or fruit to be protected.

The term "blend" is intended to mean a uniform combination of the hompolymer LDPE and of the requisite ethylene copolymer.

O-halopyridyl phosphate insecticides employed in articles of the present invention are of the formula:

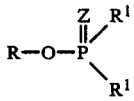

wherein R represents halopyridyl, Z represents a member of the group consisting of oxygen and sulfur, and $R^1$ represents a member of the groups consisting of lower alkoxy, amino and lower alkylamino, most preferably O,O-diethyl-3,5,6-trichloro-2-pyridyl phosphorothioate, commonly known as chlorpyrifos. Chlorpyrifos is commercially available as Dursban ® insecticide, trademark of The Dow Chemical Company, Midland, Mich. Methods for making the O-halopyridyl phosphates are disclosed in U.S. Pat. No. 3,244,586, whose preparative teachings are incorporated herein by reference. The hereinabove mentioned compounds are well known to those skilled in the art. The O-halopyridyl phosphate insecticide is generally present in the composition of the present invention in insectiticidally effective amounts in a concentration of about 0.1 to about 15 percent by weight, preferably from about 1.0 to about 2.0 percent by weight.

The term "pigment" is intended to mean substances which, when added to compositions for preparing articles of the present invention, impart an opaque or translucent appearance to the article. Generally, the pigment is an insoluble solid which, when dispersed in a binder or medium, tends to remain insoluble. The average ultimate particle size of the pigments can range from about 0.01–1.0 μm (micrometers) in diameter. Representative white pigments include but are not limited to zinc oxide, zinc sulfide, lithopane, lead pigments, antimony oxide, lead carbonate (basic white lead), lead sulfate (basic), and preferably titanium dioxide. Representative black pigments include carbon blacks. Colored pigments include inorganic pigments such as iron oxides and cadmiums, or organic pigments such as Pigment Green and azo compounds such as those described in the Encyclopedia of Chemical Technology, 3rd Ed. Volume 17, Pigments, John Wiley and Sons, Inc., New York, pages 790–864, (1982) and in the Concise Encyclopedia of Chemical Technology, John Wiley and Sons, Inc., New York, pages 887–892, (1985), whose preparative teachings are incorporated herein by reference. Preferably, the pigment imparts a blue color to the shroud. The amount of pigment employed in the shrouds of the present invention can range from about 0.1 to about 2.0 percent by weight.

The term "ultraviolet (UV) light stabilizer" is a substance that protects light sensitive materials from degradation by UV light. Light initiated oxidation is frequently responsible for much of the light induced damage of polymeric materials. Where the article is extruded at high temperatures, the ultraviolet absorber should have a correspondingly low volatility. Selection of the UV stabilizer depends upon the composition of the article, its thickness and processing conditions. The amount of the UV stabilizer in the article should be a UV stabilizing amount effective to stabilize the article against ultraviolet rays. Concentration of the UV stabilizer can range between about 0.25 percent to about 3 percent by weight. Representative UV stabilizers which can be employed in articles of the present invention include but are not limited to hindered-amine light stabilizers (HALS) such as bis-(2,2,6,6-tetramethyl-4-piperidinyl)sebacate, Chimassorb 944 and Tinuvin 622; nickel chelates such as nickel dialkyldithiocarbamates; and 2-hydroxybenzophenones such as 2,4-dihydroxybenzophenone, 2-hydroxy-4-methoxybenzophenone, 2-hydroxy-4-n-octyloxybenzophenone, 2-hydroxy-4-isooctyloxybenzophenone, 2-hydroxy-4-dodecyloxybenzophenone, 2,2'-dihydroxy-4-methoxybenzophenone, 2,2',4,4'-tetrahydroxybenzophenone, 2,2-dihydroxy-4,4'-dimethoxybenzophenone, and 2-hydroxy-4-methoxy-5-sulfobenzophenone; 2-(2'-hydroxyphenyl)-benzotriazoles such as 2-(2'-hydroxy-5-methylphenyl)-benzotriazole.

Such UV stabilizers are known and described in the hereinbefore referenced Encyclopedia of Chemical Technology, Volume 23, pages 615–627, whose preparative teachings are incorporated by reference.

The homopolymer, low density polyethylene (LDPE) is a polymer known to those skilled in the art. Generally, these polymers are made by polymerization of ethylene at high pressures aided by initiators or catalysts. Film made from this polymer is used primarily for packaging. In its other fabricated forms, low density polyethylene is used in injection moldings, coatings and extrusions. Low density polyethylene has desirable physical properties such as tensile strength for blowing or casting into film. The concentration of the homopolymer, low density polyethylene in the composition of the present invention can range from about 5 percent by weight to about 95 percent by weight of the total composition, preferably from about 25 percent to about 75 percent, most preferably about 50 percent.

Representative comonomers of salts of said unsaturated acids and of esters of said unsaturated mono- or dicarboxylic acids wherein the alcohol moiety has 1 to 8 carbon atoms include but are not limited to the ionomers of acrylic acid and methacrylic acid.

The ethylene copolymers suitable for the composition of the present invention are copolymers with at least one comonomer which is a carboxylic acid having 3 to 5 carbon atoms. Representative carboxylic acid comonomers of 3 to 5 carbon atoms include but are not limited to acrylic acid and methacrylic acid, preferably acrylic acid. Salts of said carboxylic acid comonomers include ammonium or salts of alkaline or alkali earth metals, such as sodium, potassium and calcium.

The esters of such carboxylic acid comonomers can have between about 1 to about 8 carbon atoms. Representative esterified comonomers include but are not limited to methyl acrylate, ethyl acrylate, isobutyl acrylate, and n-butyl acrylate, hexyl acrylate, octyl acrylate and the like.

In accordance with the above, suitable ethylene copolymers include ethylene/acrylic acid and its salts or ionomers; ethylene/methacrylic acid and its ionomers; ethylene/methyl acrylate; ethylene/ethyl acrylate; ethylene/isobutyl acrylate; ethylene/normal butyl acrylate; preferably ethylene/acrylic acid.

The ethylene content of the copolymer is from about 80 to about 99.5 percent by weight, and the comonomer content is from about 0.5 to about 20 percent by weight. The preferred ethylene and comonomer level is from about 98 to about 92 percent and from about 2 to about 8 percent by weight, respectively. The most preferred ethylene and comonomer content is from about 96 to about 94 percent and from about 4 to about 6 percent, respectively. A mixture of two or more ethylene copolymers can be used in the blends of the present invention in place of a single copolymer as long as the average values for the comonomer content will be within the above-indicated range.

Three to five carbon carboxylic acid comonomers and methods for making these comonomers used in the copolymer are known. See, for example, the methods taught in U.S. Pat. No. 4,599,392 for making copolymers of ethylene/acrylic acid. Certain ethylene/acrylic copolymers are commercially available in formulations such as Primacor ® 1430 (9 percent acrylic acid), trademark of The Dow Chemical Company, Midland, Mich. The concentrations of ethylene/acrylic acid copolymer in the composition of the present invention can range from about 2.5 percent by weight to about 95 percent by weight of the total composition, preferably from about 25 percent to about 75 percent by weight, most preferably about 50 percent.

The weight ratios of the LDPE to the ethylene copolymer in the composition of the present invention can range from about 95:5 (LDPE:ethylene copolymer) to about 5:95, preferably from about 75:25 to about 25:75, most preferably about 50:50. The concentrations of ethylene/acrylic acid copolymer in the composition of the present invention can range from about 2.5 percent by weight to about 95 percent by weight of the total composition, preferably from about 25 percent to about 75 percent by weight, most preferably about 50 percent.

The comonomers, such as acrylic acid, are provided for in the compositions of the present invention in a concentration effective to control the migration of the O-halopyridyl phosphate insecticide from polymers made from said composition. Generally, such concentrations of the comonomer can range from about 0.5 percent to about 20 percent by weight of the total composition, preferably in the range of about 2 percent to about 8 percent by weight, more preferably about 4 percent by weight.

The compositions of the present invention are preferably prepared by dry blending together low-density polyethylene and a copolymer such as ethylene/acrylic acid, and then by adding the O-halopyridyl phosphate insecticide, the UV stabilizer and the pigment. The dry blend is heated to a temperature below the melting temperature of either polymer in the blend but above the melting point of the O-halopyridyl phosphate insecticide to absorb the said insecticide onto the polymer blend. Such temperatures for absorbing said insecticide onto the polymer blend can range from about 50° C. to about 90° C., preferably from about 80° C. to about 85° C. The composition thus formed can be extruded into articles such as pellets, sheets, films, bags or shrouds.

In an alternative embodiment, the O-halopyridyl phosphate insecticide, pigment and UV stabilizer can be incorporated into the polymer by heating the LDPE pellets to a suitable temperature as described hereinbefore, wetting the heated pellets with the insecticide, the pigment and the UV stabilizer, and cooling the LDPE pellets. The thus treated LDPE pellets are then mixed with a copolymer, such as ethylene/acrylic acid.

Alternatively, the insecticide, the UV stabilizer and the pigment can be added first to the copolymer, and the resultant copolymer containing the insecticide, UV stabilizer and pigment is then mixed with the homopolymer LDPE.

In another alternative embodiment, the homopolymer LDPE and the copolymer are melted or molded together using extrusion processes such as side-arm extrusion. The O-halopyridyl phosphate insecticide, UV stabilizer and pigment are injected onto a molten blend of LDPE and EAA using an injection procedure such as side-arm injection.

The size of the polymer pellets can range in diameter from about 1/16 to about ½ inch, more preferably from about 1/16 to about ¼ inch. In certain applications the pellets can be ground into a powder of a particle size smaller than 1/16 inch. The pellets can be extruded into a variety of shapes due to inherent thermoformability typical of thermoplastics. Thus, the pellets can be spherical, cylindrical, strands, sheets, films, cast film from a slit die or blown film from an annular die.

The thickness of films prepared from the compositions of the present invention can range from about 0.5 mil to about 250 mil, preferably from about 0.5 mil to about 4 mil, most preferably about 1 mil. One mil equals 1/1000=0.002 inch=0.00254 centimeters (cm) or 0.0254 millimeters (mm).

Fruits to which the articles of the present invention can be applied include grapes, citrus fruits such as grapefruits and oranges, other fruits such as bananas, apples, cherries and melons, such as watermelon, and date palms. Vegetables for articles of the present invention can be utilized include tomato plants and tomato clusters, beans, peas, broccoli and squash. Generally, the articles can be applied to the plant or plant parts upon formation of the fruit or vegetable and maintained in place until maturation thereof.

EXAMPLE 1

The Absorption Rate of Chlorpyrifos Onto Low Density Polyethylene and Ethylene/Acrylic Acid Pellets A constant temperature oven is set at 85° C. by using a thermowatch controller and an infrared heat lamp. A wide mouth quart jar containing 247.5 g of 749 low density polyethylene (LDPE) or an equivalent amount of Primacor ® 1430 pellets is placed into the oven and left overnight. Primacor ® is a copolymer of ethylene/acrylic acid (EAA) containing 9 percent (%) by weight acrylic acid. Two and one-half grams of liquid Dursban ® insecticide heated to 50° C. are added to each jar to give a calculated concentration of 1 percent chlorpyrifos in the polymer. The Dursban ® insecticide contains 99 percent chlorpyrifos and 1 percent inert ingredients. The jar is shaken initially, returned to the oven, and then removed every 5 minutes and reshaken. A first sample of 10 pellets is taken from the jar after 15 minutes. The pellets are placed on an ice water bath for 1 minute, removed with tweezers and placed into a 50 ml beaker. The pellets are rinsed with 5 mls of acetone to remove excess water. The pellets are rinsed with 5 mls of methylene chloride to remove chlorpyrifos coated on the pellet surface. The solvent is decanted after each rinse and the pellets are dried by blowing nitrogen over them for three minutes. The pellets are weighed on an analytical balance, placed into a 2 ounce bottle and the chlorpyrifos absorbed by the pellets is extracted by shaking the pellets with 20 mls of chloroform on an automatic shaker overnight. The chloroform extract, after appropriate dilution, is measured at 292 nanometers wave length on an ultraviolet (UV) spectrophotometer. The absorbence of the sample extract is compared to a standard curve of absorbence from a known concentration of chlorpyrifos in chloroform. The absorption rate for the Primacor ® 1430 pellets is determined in the same manner as the LDPE. The results are shown in Table 1.

hour period. The jars are periodically removed, shaken, and replaced during this period, after which, the chlorpyrifos is absorbed by the pellets.

The polymer samples are removed from the oven and allowed to cool. The cooled samples are extruded and blown into a tubular film using a ¾ inch Haake extruder with a length/diameter (L/D) ratio of 26/1. The extrusion conditions are as follows:

| Frost Line, inches | 4 |
|---|---|
| Output, grams/minute | 23.7 |
| Layflat, inches | 3⅛ |
| Lines Speed, feet/minute | 18.4 |
| Revolutions per Minute (RPM) | 45 |
| % Load | 29 |
| Blow Up Ratio | 2:1 |
| Thickness, mils | 1.0 |
| Zone 1, Temperature °F. | 240/255 |
| Zone 2, Temperature °F. | 270/275 |
| Zone 3, Temperature °F. | 290/310 |
| Die Temperature °F. | 300/310 |
| Melt Temperature °F. | 250 |

Approximately 15 feet of the tubular film from each sample is draped over a lattice rack and secured. Dry air is blown through the tube briefly to insure the tube is open. Samples are clipped initially from each tube of film and then samples are clipped periodically thereafter and analyzed for chlorpyrifos using the procedures as described in Example 1 to determine the rate of migration of chlorpyrifos from the film.

The half-life of chlorpyrifos in the film sample is

TABLE 1

Calculated Percentage (%) of Chlorpyrifos Absorbed Onto LDPE or the Copolymer Ethylene/Acrylic Acid (EAA) at 85° C.

| Time Chlorpyrifos was Contacted with Pellets | Calculated % Weight of Chlorpyrifos Added to Polymer | Actual Weight % Chlorpyrifos Found in LDPE | Actual Weight % Chlorpyrifos Found in Copolymer EAA | % of Chlorpyrifos Absorbed** onto LDPE | % of Chlorpyrifos Absorbed** onto Copolymer EAA |
|---|---|---|---|---|---|
| 0 minutes | 1.0 | 0.0 | 0.0 | 0.0 | 0.0 |
| 15 minutes | 1.0 | 0.64 | 0.71 | 71.1 | 80.7 |
| 30 minutes | 1.0 | 0.76 | 0.80 | 84.4 | 90.9 |
| 45 minutes | 1.0 | 0.86 | 0.85 | 95.6 | 96.6 |
| 60 minutes | 1.0 | 0.91 | 0.84 | 101.1 | 95.5 |
| 90 minutes | 1.0 | 0.89 | 0.83 | 98.9 | 94.3 |
| 120 minutes | 1.0 | 0.92 | 0.95 | 102.2 | 108.0 |
| 150 minutes | 1.0 | 1.07 | 0.86 | 118.9 | 97.7 |
| 180 minutes | 1.0 | 0.90 | 0.88 | 100.0 | 100.0 |

**The "% absorbed" values are determined assuming that the maximum absorption of chlorpyrifos by the LDPE is 0.90% and the maximum absorption by the Copolymer EAA is 0.88% by weight based on a time of 180 minutes.

EXAMPLE 2

Migration Rate of Chlorpyrifos From Films Derived From Blends of LDPE and Ethylene/Acrylic Acid (EAA)

Seven polymer samples are prepared for evaluation. Chlorpyrifos from a formulation of Dursban ® insecticide, equaling one percent by weight in each sample, is added to pellets of 749 LDPE, Primacor ® 1430 (EAA), and to blends of the above resins consisting of 0.5 percent, 1.0 percent, 2.0 percent, 4.0 percent and 6.0 percent as acrylic acid in final blend of the LDPE and EAA. Each sample is placed in individual glass jars, the jars are sealed and heated in an oven at 85° C. over a 24 determined by plotting the percent of chlorpyrifos remaining in the film over the time in days by the following formula:

| % Chlorpyrifos Remaining in Film = $W_i/W_o \times 100$ where $W_o$ = percent by % weight of chlorpyrifos initially and $W_i$ = weight of chlorpyrifos for any time thereafter in days. |
|---|

The half-life is the point in time, measured in days, when 50 percent of the active ingredient, chlorpyrifos, remains in the film sample. The results of the analysis for a 1.0 mil film are shown in Tables 2 and 3.

TABLE 2

Half-life of Chlorpyrifos in 1.0 mil Films of LDPE, LDPE/EAA Blends and EAA

| Sample | 100% LDPE, 0% as Acrylic Acid | LDPE/EAA Blend, 0.5% as Acrylic Acid | LDPE/EAA Blend, 1.0% as Acrylic Acid | LDPE/EAA Blend, 2.0% as Acrylic Acid | LDPE/EAA Blend, 4.0% as Acrylic Acid | LDPE/EAA Blend, 6.0% as Acrylic Acid |
|---|---|---|---|---|---|---|
| % Increase in half-life of Chlorpyrifos | 0 | 3 | 11 | 24 | 45 | 66 |
| Half-Life for Chlorpyrifos in days | 3.8 | 3.9 | 4.2 | 4.7 | 5.5 | 6.3 |
| Composition and Quantity of Sample Prepared | 750 g LDPE | 41.67 g EAA + 708.33 g LDPE | 83.33 g EAA + 666.67 g LDPE | 166.67 g EAA + 583.33 g LDPE | 333.33 g EAA + 416.67 g LDPE | 500.00 EAA + 250.00 LDPE |

TABLE 3

Half-life of Chlorpyrifos in Selected Polymer Films

| Concentration of Acrylic Acid in blends of LDPE and EAA | Half-life of Chlorpyrifos in Film | Increase in Half-life |
|---|---|---|
| 0.0% | 3.8 days | 0.0% |
| 0.5% | 3.9 days | 3.0% |
| 1.0% | 4.2 days | 11.0% |
| 2.0% | 4.7 days | 24.0% |
| 4.0% | 5.5 days | 45.0% |
| 6.0% | 6.3 days | 66.0% |

EXAMPLE 3

Chlorpyrifos impregnated, plastic sleeves protecting Deglet Noor date bunches are tested for control of moths.

The plastic shrouds are white, 4 mils in thickness, 24 inches in diameter and thirty-six inches long. Perforated sleeves have 1 inch diameter holes in rows 5 inches apart. The shrouds containing 2 percent by weight chlorpyrifos are prepared from a 50:50 blend of LDPE and a copolymer of ethylene/acrylic acid (EAA) containing 9 percent by weight acrylic acid. Shrouds are installed by pulling the shroud up from the bottom of the bunches and until 5 to 6 inches of the shroud remain below the bunches and are kept in the bunches for 12 weeks or until the fruit reaches maturity for harvesting. The open end of the top was wrapped around the bunch stalk and secured by duct tape.

The study begins about August 1 to coincide with the commercial wrapping of the date bunches with paper when the dates are in the kimri and khalal stages. The kimri stage, as defined by R. A. Nixon and J. B. Carpenter, 1978 U.S.D.A., Agric. Bull. Information No. 207, is the first stage of a date in which a date grows most rapidly and is distinguished by its green color. The khalal stage is the second stage of date development when the date reaches maximum size and the green color is replaced by red or yellow or combination of the two. Analysis of the mature dates indicates the dates to be nearly free of moth infestation.

EXAMPLE 4

A second study is conducted as described in Example 3 except for the time at which the shrouds are installed. The study is initiated on about September 4 at the inception of the development of the rutab stage as moth ovipositional activity is increasing based on egg trap counts. The rutab stage is the third stage of development when the tip first begins to soften and lose its khalal color. These same fine results are obtained as in Example 3.

What is claimed is:

1. A method for retarding the migration of an O-pyridyl phosphate insecticide of the formula

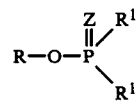

wherein

R represents halopyridyl, Z represents a member of the group consisting of oxygen and sulfur, and $R^1$ represents a member of the group consisting of lower alkoxy, amino and lower akylamino from a low density polyethylene matrix which comprises incorporating into the matrix an ethylene copolymer having at least one comonomer which is an unsaturated 3 to 5 carbon atom carboxylic acid, salt or ester thereof present in a concentration of from about 0.5 to about 20 weight percent of the total composition.

2. The method of claim 1 wherein the O-halopyridyl phosphate insecticide is chlorpyrifos.

3. The method of claim 1 wherein the comonomer is acrylic acid.

4. The method of claim 3 wherein the concentration of the acrylic acid is in the range of about 2 to about 8 percent by weight of the composition.

* * * * *